United States Patent
Auguste et al.

(10) Patent No.: US 9,452,086 B2
(45) Date of Patent: *Sep. 27, 2016

(54) HYDROCELLULAR ABSORBENT DRESSING, AND USES THEREOF FOR THE TREATMENT OF CHRONIC AND ACUTE WOUNDS

(75) Inventors: Stephane Auguste, Ruffey les Echirey (FR); Jean-Marc Pernot, Dijon (FR); Anne-Sophie Danerol, Dijon (FR); Aurélie Charre, Montanay (FR)

(73) Assignee: LABORATOIRES URGO, Chenove (FR)

( * ) Notice: Subject to any disclaimer, the term of this patent is extended or adjusted under 35 U.S.C. 154(b) by 48 days.

This patent is subject to a terminal disclaimer.

(21) Appl. No.: 14/111,850

(22) PCT Filed: Apr. 13, 2012

(86) PCT No.: PCT/FR2012/050811
§ 371 (c)(1),
(2), (4) Date: Jan. 3, 2014

(87) PCT Pub. No.: WO2012/140377
PCT Pub. Date: Oct. 18, 2012

(65) Prior Publication Data
US 2014/0142526 A1    May 22, 2014

(30) Foreign Application Priority Data
Apr. 15, 2011 (FR) ........................ 1153325

(51) Int. Cl.
*A61F 13/02* (2006.01)
*A61F 13/00* (2006.01)

(52) U.S. Cl.
CPC ......... *A61F 13/0206* (2013.01); *A61F 13/022* (2013.01); *A61F 13/023* (2013.01);
(Continued)

(58) Field of Classification Search
CPC .............. A61F 2013/00119; A61F 13/0206; A61F 13/0213; A61F 13/022; A61F 2013/00225; A61F 2013/00702; A61F 2013/00778; A61F 2013/00782; A61F 13/0074; A61F 2013/00744; A61F 2013/00855; A61F 2013/00097; A61F 2013/00404; A61F 2013/00761; A61F 2013/00523; A61F 2013/548; A61F 2013/00604; A61F 2013/00608; A61F 13/023; A61F 13/0246; A61F 13/0279; A61F 13/0283; A61F 2013/00229; A61F 2013/00719; A61F 2013/00723; A61F 2013/0077; A61F 2013/53113; A61F 2013/530802; A61F 13/0226; A61F 203/53463

USPC .......... 602/41, 46, 58; 427/2.31; 442/22, 26; 604/365

See application file for complete search history.

(56) References Cited

U.S. PATENT DOCUMENTS

| | | |
|---|---|---|
| 4,921,704 A | 5/1990 | Fabo |
| 6,023,008 A | 2/2000 | Mahoney et al. |

(Continued)

FOREIGN PATENT DOCUMENTS

| | | |
|---|---|---|
| EP | 0251810 | 1/1988 |
| EP | 0299122 | 1/1989 |

(Continued)

OTHER PUBLICATIONS

Translation of WO 2008/146529 A1 (JP2008055878) to Oka.*

*Primary Examiner* — Peter S Vasat
(74) *Attorney, Agent, or Firm* — Hamre, Schumann, Mueller & Larson, P.C.

(57) ABSTRACT

The present invention relates to an absorbent dressing comprising a breathable impermeable substrate (4) and an absorbent foam (2), which is particularly suitable for use in the care of chronic or acute wounds.

The invention relates to a dressing comprising an absorbent foam (2) and a protective substrate (4) that is impermeable to fluids, but permeable to water vapor, said substrate being formed by assembling a film (4a) and an openwork reinforcement that is coated with an adhesive silicone gel (4b) without blocking the openings in the reinforcement. In addition, the dressing comprises a non-absorbent web (5) which is disposed between the absorbent foam (2) and the substrate (4), which adheres to the adhesive silicone gel coating on the reinforcement, and which adheres to the absorbent foam (2).

19 Claims, 2 Drawing Sheets

(52) U.S. Cl.
CPC ....... *A61F13/0213* (2013.01); *A61F 13/0246* (2013.01); *A61F 13/0279* (2013.01); *A61F 13/0283* (2013.01); *A61F 2013/0077* (2013.01); *A61F 2013/00225* (2013.01); *A61F 2013/00229* (2013.01); *A61F 2013/00604* (2013.01); *A61F 2013/00702* (2013.01); *A61F 2013/00719* (2013.01); *A61F 2013/00723* (2013.01); *A61F 2013/00774* (2013.01); *A61F 2013/00778* (2013.01); *A61F 2013/00782* (2013.01)

(56) References Cited

U.S. PATENT DOCUMENTS

| | | | |
|---|---|---|---|
| 6,096,942 | A | 8/2000 | Hack |
| 6,881,875 | B2 * | 4/2005 | Swenson .................. 602/46 |
| 2004/0241214 | A1 * | 12/2004 | Kirkwood et al. ........... 424/445 |
| 2009/0216168 | A1 | 8/2009 | Eckstein |
| 2010/0292626 | A1 | 11/2010 | Gundersen et al. |
| 2012/0095380 | A1 | 4/2012 | Gergely et al. |

FOREIGN PATENT DOCUMENTS

| | | |
|---|---|---|
| EP | 0300620 | 1/1989 |
| EP | 0358412 | 3/1990 |
| EP | 0392788 | 10/1990 |
| EP | 0420515 | 4/1991 |
| WO | WO 93/04101 | 3/1993 |
| WO | WO 94/29361 | 12/1994 |
| WO | WO 96/01659 | 1/1996 |
| WO | WO 96/16099 | 5/1996 |
| WO | WO 2004/064879 | 8/2004 |
| WO | WO 2004/074343 | 9/2004 |
| WO | WO 2008/012443 | 1/2008 |
| WO | WO 2008/146529 | 12/2008 |
| WO | 2009130485 | 10/2009 |
| WO | WO 2010/147533 | 12/2010 |

* cited by examiner

FIG.3

HYDROCELLULAR ABSORBENT DRESSING, AND USES THEREOF FOR THE TREATMENT OF CHRONIC AND ACUTE WOUNDS

The present invention relates to a dressing comprising a breathable impermeable protective substrate and an absorbent foam, and also to the use thereof in the care of chronic wounds, such as ulcers or eschars, or acute wounds, such as burns.

The hydrocellular absorbent dressings used for treating wounds generally consist of the assembly of an absorbent foam and a breathable impermeable protective substrate. These dressings can comprise an adhesive border which makes it possible to secure them to the healthy skin which surrounds the wound. They can also comprise an interface layer positioned on the absorbent foam, for avoiding direct contact between the foam and the wound.

For example, the Cellosorb® Contact Adhesive absorbent dressing comprises a highly breathable elastic polyurethane nonwoven protective substrate, an absorbent polyurethane foam placed at the center of the substrate, and a discontinuous interface layer which covers the foam. The interface facilitates the non-traumatic application and removal of the dressing through its micro-adhesion properties. The Cellosorb® Contact Adhesive product comprises a side strip covered with an acrylic adhesive. However, the acrylic adhesives applied to the border of dressings have a non-optimal tolerance for perilesional skin which is particularly fragile in the case of chronic wounds.

In the care of chronic and acute wounds, it is preferable to use dressings in which the side strip is covered with a silicone adhesive, which is more friendly to the perilesional skin. However, silicone adhesives are totally occlusive, so that it is necessary to apply them discontinuously in order to ensure good breathability of the dressing. However, the discontinuous application of the silicone adhesive results in too great a reduction in its capacity to adhere to the other materials constituting the dressing, in particular to the absorbent materials, and more particularly in a moist environment.

The production of absorbent dressings which use a silicone adhesive must therefore meet complex specifications and reconcile contradictory characteristics. The main criteria that the dressing must establish are essentially those of having good breathability while at the same time avoiding the risks of leaking and of maceration, of being impermeable to liquids and to bacteria, of being breathable (i.e. permeable to water vapor), of remaining cohesive when it is removed, and of being easy to manufacture.

The dressing must also be easy to apply and remain in place over time for as long as possible without being detrimental to the perilesional skin, have a high absorption capacity, and not impair the healing of the wound when it is removed. The dressing must also mold to the morphology of the patient and be compatible with the complimentary use of a support system. It must also be as flexible as possible, and not become stiff during the absorption of wound exudates.

The choice of the materials which constitute the dressing, the arrangement of the materials with respect to one another, and the means for assembling the latter are very complex if all these properties are to be obtained at the same time.

The only solution proposed to date for obtaining a dressing comprising a cohesive, breathable, impermeable silicone adhesive has consisted in crosslinking the adhesive silicone gel on just one face of a perforated polyurethane film, while keeping the perforations of the film open. The substrate that is coated with silicone adhesive is secured to the substrate of the dressing with an acrylic adhesive or by heat-sealing.

In the Mepilex® Border product, for example, the perforated polyurethane film that is coated with adhesive silicone gel is used as an interface layer. A discontinuous layer of adhesive silicone gel therefore covers both the absorbent foam previously placed at the center of the substrate film, and the side strip of the substrate intended to adhere to the skin. In the same way, in application WO 2010/147533, a discontinuous layer of silicone adhesive covers an absorbent polyurethane foam and the substrate. This discontinuous layer consists of a perforated polyurethane film that is coated on just one side with silicone gel. This discontinuous structure makes it possible to avoid having to secure the silicone gel, once crosslinked, to the absorbent layer of the dressing. Indeed, the silicone gel once crosslinked cannot be secured in a long-lasting manner to an absorbent foam commonly used in the manufacture of a dressing.

However, in this dressing structure, the silicone gel is in direct contact with the wound. The fact that the silicone adhesive covers the entire surface of the dressing does not make it possible to specifically adapt the interface layer which may cover the surface of the absorbent foam; consequently, a dressing in which only the side strip is covered with silicone adhesive, and the absorbent foam is in direct contact with the wound, has been proposed in document US 2010/0292626. To produce this structure, a polyurethane film that is coated with silicone gel is cut in the shape of the side strip and is then adhesively bonded to a substrate film with an acrylate adhesive. In this dressing, the polyurethane film is covered with a continuous silicone gel layer, while the acrylate adhesive is coated discontinuously. The production of this dressing is, however, complex because of the steps of cutting and centring the various constituents.

There is therefore a need to manufacture a dressing which is impermeable to liquids but highly permeable to water vapor and which uses a silicone adhesive, said dressing being easier to manufacture than the prior art dressings of this type, and remaining cohesive when it is removed from the wound.

The applicant has found a novel means for securing an absorbent foam to a substrate that is coated with a silicone gel which makes it possible to obtain a level of cohesion of the various materials assembled which is sufficient when the dressing is dry but also when it is loaded with wound exudates. The dressing is also easier to manufacture than the prior art dressings which use silicone adhesives. By virtue of this dressing, it is not obligatory to cover the entire surface of the dressing with the adhesive silicone gel in order to simplify the process for manufacturing the dressing, so that another interface layer which is more wound-friendly can optionally be applied to the foam.

DETAILED DESCRIPTION

A subject of the invention is thus a dressing comprising an absorbent foam and a protective substrate that is impermeable to fluids, but permeable to water vapor, said substrate being formed by assembling a continuous film and an openwork reinforcement that is coated, on at least one of its faces, with an adhesive silicone gel without blocking the openings in the reinforcement, said reinforcement covering the entire surface of the film, said dressing also comprising a non-absorbent web which is inserted between said absorbent foam and said substrate, which web adheres to the adhesive silicone gel that is coated onto said reinforcement, and which is secured to the absorbent foam, preferably only along its periphery.

The non-absorbent web is an essential element of the invention since a substrate that is coated with a silicone gel over the entire surface of one of its faces, and in particular discontinuously, does not adhere to an absorbent foam. The foam also cannot be assembled, using an acrylate adhesive, to the substrate that is coated with silicone gel.

Figure 1:
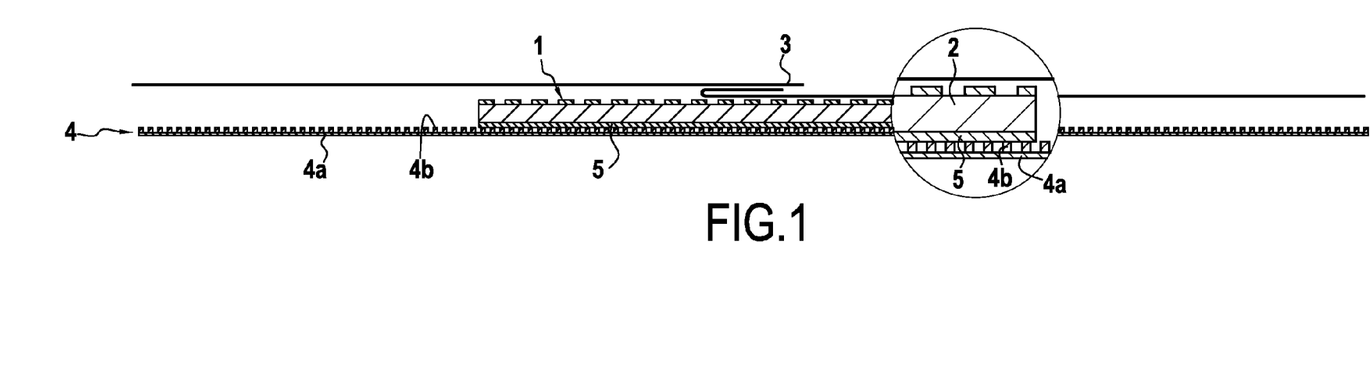
FIG. 1 represents a cross section view of an embodiment of the present invention comprising an absorbent foam, and a protective substrate being formed by assembling a continuous film and an openwork reinforcement. The reinforcement is coated with an adhesive silicone gel. A non-absorbent web is inserted between the absorbent foam and the protective substrate. The absorbent foam covered with a discontinuous interface layer that is protected by a peel-off protector.
Figure 2:
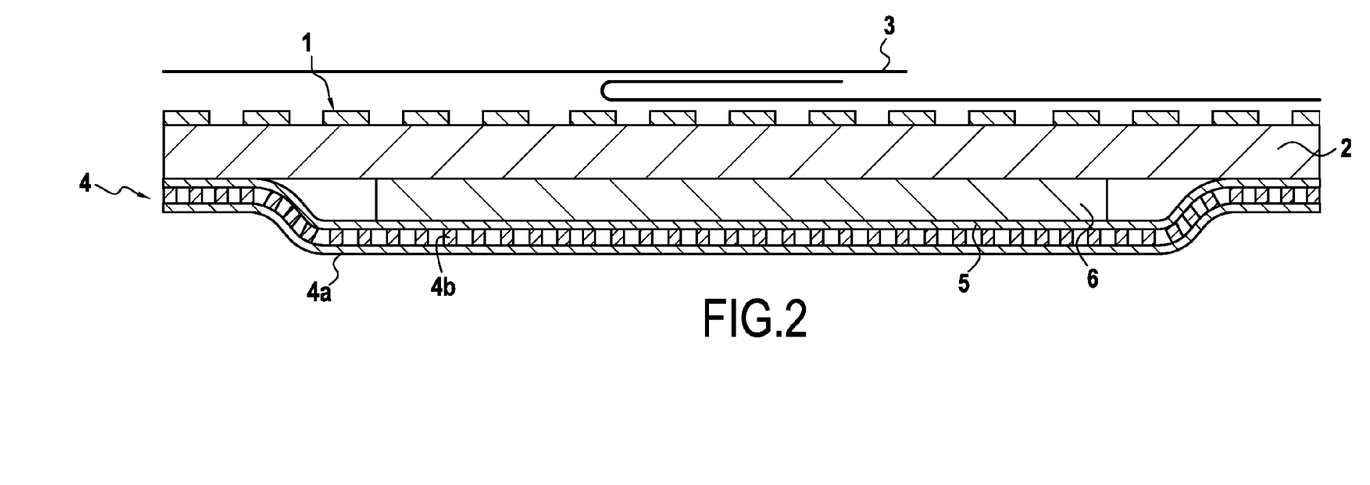
FIG. 2 is a cross section view of an embodiment of the present invention comprising an absorbent nonwoven that is inserted between a non-absorbent web and an absorbent foam. The substrate has the same size as the absorbent foam.
Figure 3:
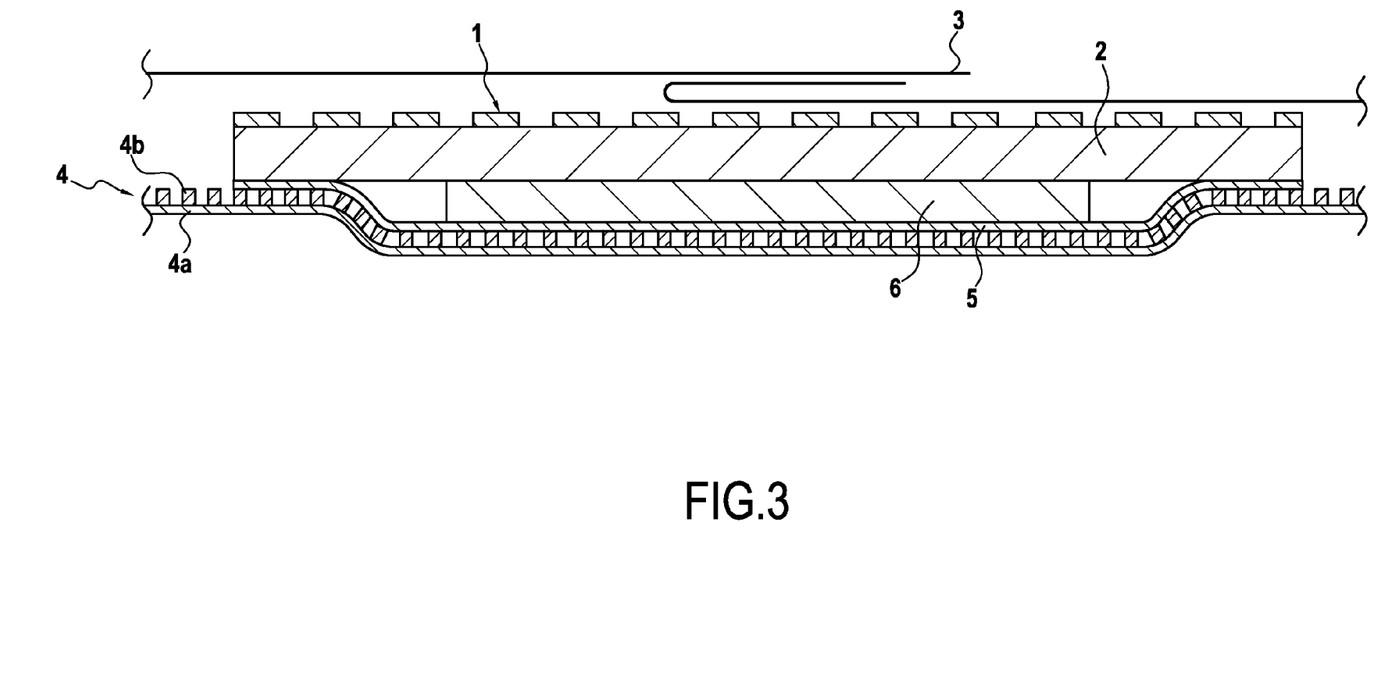
FIG. 3 is a cross section view of an embodiment of the present invention comprising a protective substrate, and an absorbent nonwoven that is inserted between a non-absorbent web and an absorbent foam. The substrate is wider than the absorbent foam and the non-absorbent web so as to form adhesive margins or borders.

Such dressings are, for example, described by diagrammatic views in appended FIGS. 1 to 3. In these figures, the dressing is represented in cross section.

In FIG. 1, an absorbent foam 2 is covered, on the side facing the wound, with a discontinuous interface layer 1 protected by a peel-off protector 3.

The substrate 4 is formed by assembling a film 4a that is impermeable to liquids, but permeable to water vapor, and an openwork reinforcement that is coated with an adhesive silicone gel 4b without blocking the openings in the reinforcement. The substrate 4 is secured to the absorbent foam 2 by insertion of a non-absorbent web 5.

In FIGS. 2 and 3, an absorbent nonwoven 6 is inserted between the web 5 and the absorbent foam 2. The web 5 is secured along its periphery to the absorbent foam 2 in such a way as to encase the absorbent nonwoven 6, the size of which is smaller than that of the absorbent foam.

In FIG. 2, the substrate has the same size as the absorbent foam, whereas in FIGS. 1 and 3, the substrate is wider than the absorbent foam and the non-absorbent web so as to form adhesive margins or borders which can adhere to the skin.

The substrate is preferably impermeable to fluids and to external pathogenic microorganisms, while at the same time providing permeability to water vapor, so as to avoid both contact of the wound with external liquids and bacteria and maceration of the wound. This is then referred to as a "breathable impermeable substrate".

The substrate is preferably thin and flexible, so as to mold better to the shape of the body and to follow the movements without risk of detaching. The substrate is advantageously conformable. Its thickness can be between 100 and 600 µm, and preferably between 250 and 500 µm.

The substrate which is part of the dressing according to the invention consists of a continuous film 4a and an openwork reinforcement that is coated with an adhesive silicone gel 4b without blocking the openings of the reinforcement. The film is continuous in the sense that it has not undergone a perforation step.

The film can be replaced with a foam/film complex or a textile/film complex. Among the usable films, mention may be made, by way of example, of polyether urethane, polyetheramide or polyether ester films.

The thickness of the film is, for example, between 5 and 200 microns, preferably between 10 and 75 microns and more preferably between 10 and 50 microns.

The continuous film is impermeable to liquids, but permeable to water vapor. The continuous film may be a breathable impermeable film or complex previously mentioned, such as those commonly used for manufacturing absorbent dressings. The film advantageously has a moisture vapor transmission rate (MVTR) greater than 3000 g/m²/24 hours, preferably greater than or equal to 7000 g/m²/24 hours and more preferably greater than or equal to 10 000 g/m²/24 hours. The openwork reinforcement is coated with a silicone compound without blocking the openings of the reinforcement. This reinforcement thus coated is advantageously chosen in such a way that the value of the moisture vapor transmission rate of the substrate remains satisfactory, in particular greater than or equal to 4000 g/m²/24 hours, preferably greater than or equal to 5000 g/m²/24 hours. A technique for measuring the moisture vapor transmission rate in liquid contact is described in standard NF-EN 13726-2 (Chapter 3.3).

When the dressing comprises a side strip, the reinforcement makes it possible to stiffen the substrate, in such a way that it does not roll up on itself after removal of a peel-off protector optionally used to protect the foam or the interface layer, and/or the adhesive border.

The reinforcement may consist of any openwork material, such as a perforated film, a thermoplastic net, a textile, for instance a woven, a knit or a nonwoven, which is preferably elastic for a better hold of the dressing on the skin. A perforated film will, for example, be made of polyethylene or of polypropylene. A woven textile will, for example, be made of polyethylene terephthalate or of polyamide. The grammage of the reinforcement is preferably between 10 and 500 g/m², for example between 20 and 300 g/m². The reinforcement can be coated with silicone gel on one of its faces, on both its faces, or even on its entire surface. The size of the openings of the reinforcement can be between 0.1 and 5 mm, for example between 0.5 and 3 mm. The open surface of the reinforcement preferably represents from 1% to 99%, preferably from 25% to 90% and more preferably from 30% to 80% of the surface of the continuous film, and the open surface of the reinforcement once covered with silicone gel preferably represents from 10% to 99%, preferably from 10% to 60% and more preferably from 25% to 75% of the surface of the continuous film.

According to one embodiment, a knit, preferably a knit that is coated with silicone gel on its entire surface without blocking the openings of the knit, will be used. The whole of the mass of the knit is coated with silicone gel, for example by dipping the knit in a silicone gel precursor mixture.

According to another embodiment, the reinforcement is a perforated film that is coated with silicone gel on just one of its faces without blocking the perforations of the film, for example a perforated polyurethane film, which may be secured to the continuous film via heat, ultrasound, high frequency or an adhesive.

The adhesive silicone gel is a silicone compound of which the structure is crosslinked. The silicone gel exhibits a cohesion such that it does not leave residues on the skin and remains attached to the reinforcement when the dressing is removed. It can be manufactured from silicone precursors which crosslink after they have been brought into contact, following a hydrosilylation or condensation reaction. Such systems are known from the prior art, for example in documents EP-A-0 251 810, EP-A-0 300 620 or U.S. Pat. No. 4,921,704. The mixtures of precursors described in said documents comprise essentially:

- a component A which comprises at least one polydimethylsiloxane substituted with a vinyl group at each of its ends, and a platinum catalyst, and
- a component B of polydimethylsiloxane which comprises at least two hydrosilane groups.

Bringing together the two components causes a crosslinking reaction of the two functionalized polydimethylsiloxanes which advantageously takes place at ambient temperature and can be accelerated by heat.

Additives such as pigments, inhibitors or bulking fillers can be incorporated into at least one of the two components.

The precursors of the adhesive silicone gel can be chosen from the following products: Silbione RT Gel® 4712 A&B and Silbione RT Gel® 4717 A&B from Bluestar Silicones, Wacker Silgel® 612 from Wacker-Chemie GmbH, Nusil® MED-6340, Nusil® MED-6345, Nusil® MED3-6300 or Nusil® MED12-6300 from Nusil Technology, and D-7-9800® from Dow Corning.

The silicone gel is preferably chosen in such a way that the substrate has an adhesive power on skin, according to the EN 1939 method, of greater than 40 cN/cm, and preferably 45 cN/cm. A substrate sample 20 mm wide and 150 mm long is placed on the forearm. After 10 minutes, the adhesive power is measured with a dynamometer at a tensile speed of 900 mm/min with an angle of 90°.

The silicone gel is preferably applied to the openwork reinforcement without blocking the openings of the reinforcement at a grammage of between 100 and 500 g/m$^2$, preferably between 150 and 250 g/m$^2$, so as to provide a compromise between a sufficient moisture vapor transmission rate and a sufficient adhesion to the continuous film or to the skin.

By way of example, use may be made of a substrate consisting of the combination of a polyurethane film 30 μm thick which has a moisture vapor transmission rate of about 7000 g/m$^2$/24 hours, and of a 40 g/m$^2$ polyester knit that is coated with a silicone gel on its entire surface in a proportion of 200 g/m$^2$.

This substrate has a thickness of about 400 μm and an MVTR of about 5000 g/m$^2$/24 hours.

In one embodiment, the size of the substrate is greater than that of the absorbent foam and the foam is centered on the substrate so as to create adhesive borders.

The dressing according to the invention comprises a web which is inserted between the absorbent foam and the substrate, and which is intended to assemble them. This securing means is necessary since the surface of the substrate that is coated with an adhesive silicone gel does not adhere sufficiently to the absorbent foam in particular in a moist environment.

The web inserted between the absorbent foam and the substrate is a non-absorbent nonwoven of low grammage. The nonwoven may be any type of nonwoven commonly used in the field of hygiene and dressings, in particular a spun laid, carded or spun lace nonwoven. Its grammage is preferably between 15 and 50 g/m$^2$, preferably between 20 and 40 g/m$^2$.

The web is non-absorbent in the sense that it does not contain absorbent fibers such as rayon, viscose or cellulose derivatives, and that it does not contain absorbent particles.

It may comprise polyamide, polyester, polyurethane and/or polyolefin fibers. According to one embodiment, the web comprises polyethylene fibers. The fibers may be single-component fibers, or two-component fibers of core/shell or side-by-side type. A spun laid nonwoven, preferably of spun bond type, will for example be chosen.

The non-absorbent web will preferably consist of hydrophobic fibers, but it may also consist of hydrophilic fibers and have undergone a treatment to make it hydrophobic. The web may consist of several layers, insofar as its porosity is sufficient, the layer which comes into contact with the adhesive silicone gel being non-absorbent and preferably hydrophobic.

The non-absorbent web is secured to the absorbent foam over its entire surface, or preferably only along its periphery, by means of conventional securing techniques such as heat, ultrasound, high frequency, or with adhesives.

In the context of the present invention, use will be made, for example, of a spun bond nonwoven consisting of polyethylene fibers having a grammage of between 30 and 40 g/m$^2$, such as the product sold by the company Freudenberg under the name Vilmed® LSO 1040 Weiss.

In the context of the present invention, the absorbent foam may be chosen from hydrophilic absorbent foams and hydrophobic absorbent foams made absorbent via the incorporation of absorbent particles.

Hydrophilic absorbent foams and the process for manufacturing same, well known to those skilled in the art, are described in the patent applications WO 96/16099, WO 94/29361, WO 93/04101, EP 420 515, EP 392 788, EP 299 122 and WO 2004/074343. Such foams correspond, for example, to the reference MCF03 sold by the company AMS, or to the reference 562-B sold by the company Rynel.

According to one preferred version of the present invention, use will be made of a hydrophilic polyurethane foam of which the thickness is chosen according to the desired absorption capacity. In the context of the present invention, a polyurethane foam with a thickness of 1.5 to 5 mm will be most particularly preferred.

If it is designed to increase the absorption capacity of the dressing, it will be possible to combine with the foam described previously a second absorbent layer chosen from foams, absorbent textiles, for instance woven or knitted textiles, or nonwoven textiles.

According to one version of the present invention, use will be made of the combination of a foam 2, for example a hydrophilic polyurethane foam, and of an absorbent nonwoven 6. The absorbent nonwoven is preferably placed between the absorbent foam and the web, as represented in FIGS. 2 and 3. According to this variant, the absorbent nonwoven preferably has dimensions smaller than those of the foam in order to encase the absorbent nonwoven in a casing consisting of the web and the foam of which the edges are secured.

The absorbent nonwoven preferably consists of absorbent fibers such as cellulose, rayon or viscose fibers. The nonwoven is preferably obtained via the dry manufacturing method known as "airlaid".

All the bonding modes commonly used in this technology may be employed for the nonwoven of the invention: bonding by spray coating of latex, bonding by incorporation of thermal bonding fibers or powders and then heat treatment, bonding by combining these two techniques, bonding by simple compression of the fibers. The latter bonding mode, which does not call for the incorporation of thermal bonding materials or of latex, will be preferred.

According to one embodiment of the present invention, the nonwoven incorporates particles of superabsorbent polymers in a proportion of between 1% and 70% by weight, preferably from 25% 55% by weight, of the total weight of the nonwoven. The superabsorbent polymer may be chosen from acrylic polymers, including salts thereof, such as sodium polyacrylates.

According to one preferred embodiment of the present invention, use will be made of a nonwoven based on particles of superabsorbent polymers and cellulose fibers without the incorporation of thermal bonding materials or of latex, which will be covered on each of its faces with a cellulose-based web. According to another variant of the present invention, a nonwoven consisting of two cellulose-based webs, between which are incorporated particles of superabsorbent polymers alone or in combination with binding agents, may also be employed as absorbent nonwoven.

The absorbent nonwoven may also comprise superabsorbent fibers.

In the context of the present invention, use is preferably made of a nonwoven which has a thickness of between 0.5 and 3 mm and/or a grammage of between 200 and 500 g/m$^2$ and/or an absorption of greater than 5000 g/m$^2$, more preferably greater than or equal to 7000 g/m$^2$. The absorption may be measured according to standard EDANA 440.1.99.

Suitable absorbent nonwovens are, for example, sold by the company EAM Corporation under the reference Novathin®.

A discontinuous interface layer 1 intended to come into contact with the wound may advantageously be placed on the surface of the absorbent foam, facing the wound. The interface layer is discontinuous so as to allow access of the exudates to the absorbent foam; it does not detrimentally modify the wound when the dressing is removed.

According to one embodiment of the invention, the dressing does not comprise a side strip and the interface layer is microadhesive to the wound, i.e. it makes it possible to temporarily secure the dressing to the wound, and said dressing can be removed without the structure of the wound or of the perilesional skin being detrimentally modified, so that this dressing can be repositioned and facilitates nursing care. This securing can assist the care personnel or the user in covering the dressing with a support means, with an adhesive tape, with a strip or with a holding net.

The composition of the interface layer may be hydrophobic, hydrophilic or amphiphilic.

Mention may thus be made of compositions based on silicone polymers, in particular silicone gels, polyurethanes gels, elastomer-based compositions including hydrocolloids, or even hydrogels, for example poly(AMPS)-based hydrogels.

In the context of the present invention, use will most particularly be made of a discontinuous layer of composition containing an elastomer, a plasticizer and hydrocolloids. This interface layer promotes the healing process by maintaining a moist environment at the level of the wound, and also makes it possible to convey active agents, which is not the case with silicone-coated interfaces.

The elastomer may be chosen from poly(styrene-olefin-styrene) triblock block polymers optionally combined with diblock copolymers. The triblock copolymers may be poly(styrene-ethylene-butylene-styrene) (abbreviated to SEBS) block copolymers sold under the name Kraton® G1651, Kraton® G1654 or Kraton® G1652, or poly(styrene-ethylene-propylene-styrene) (abbreviated to SEPS) block copolymers.

Among the plasticizer compounds capable of being used, mention may particularly made of mineral oils, polybutenes or else phthalate derivatives. Particularly preferably, use will be made of a mineral plasticizing oil chosen from the products sold under the names Ondina®933 and Ondina®919.

As suitable hydrocolloids, mention may, for example, be made of pectin, alginates, natural vegetable gums, such as in particular karaya gum, cellulose derivatives, such as carboxymethylcelluloses and alkali metal salts thereof, such as the sodium or calcium salts, known under the reference CMC Blanose® 7H4XF, and also superabsorbent acrylic acid salt-based synthetic polymers, for instance the products sold by the company BASF under the name Luquasorb® 1003 by the company CIBA Specialty Chemicals under the name Salcare® SC91, and also mixtures of these compounds.

The elastomer-based compound including hydrocolloids can include, if necessary, one or more antioxidants, and also the surfactant Montanox® 80 or the polymer Sepinov® EMT 10, both sold by the company SEPPIC, in order to optimize the gelling speed, the wettability or the release of active agents optionally present in the composition.

If it is desired for the interface layer to be microadhesive or adhesive, the elastomer-based composition including hydrocolloids contains a tackifying product which can be chosen from tackifying resins and low-molecular-weight polyisobutylenes, or mixtures thereof. Generally, use will preferably be made of hydrogenated resins such as the Escorez® resins of the 5000 series and most particularly the Escorez® 5380 resin.

The composition may contain active ingredients which have a favorable role in the treatment of the wound. Among the substances which can be used in the context of the present invention, mention may be made, by way of example, of:

antibacterial agents, for instance silver derivatives, such as the salts of silver or of other metals (for example, silver sulfate, chloride or nitrate and silver sulfadiazine), complexes of silver or of other metals (for example, silver zeolites such as alphasan, or ceramics), metrodinazole, neomycin, polymyxin B, penicillins (amoxycillin), clavulanic acid, tetracyclines, minocycline, chlorotetracycline, aminoglycosides, amikacin, gentamicin or probiotics;

antiseptics, such as chlorhexidine, triclosan, biguanide, hexamidine, thymol, lugol, iodinated povidone, benzalkonium chloride and benzethonium;

painkillers, such as paracetamol, codeine, dextropropoxyphene, tramadol, morphine and its derivatives, corticosteroids and derivatives;

anti-inflammatories, such as glucocorticoids, non-steroidal anti-inflammatories, aspirin, ibuprofen, ketoprofen, flurbiprofen, diclofenac, aceclofenac, ketorolac, meloxicam, piroxicam, tenoxicam, naproxene, indomethacin, naproxcinod, nimesulide, celecoxib, etoricoxib, parecoxib, rofecoxib, valdecoxib, phenylbutazone, niflumic acid, mefenamic acid;

active agents which promote healing, such as retinol, vitamin A, vitamin E, N-acetylhydroxyproline, *Centella asiatica* extracts, papain, essential oils of thyme, of niaouli, of rosemary and of sage, hyaluronic acid, polysulfated oligosaccharides and their salts (in particular synthetic sulfated oligosaccharides having 1 to 4 monosaccharide units, such as the potassium salt of octasulfated sucrose or the silver salt of octasulfated sucrose), sucralfate, allantoin, urea, metformin, enzymes (for example, proteolytic enzymes such as streptokinase, trypsin or collagenase), peptides or protease inhibitors;

anesthetics, such as benzocaine, lidocaine, dibucaine, proxamine hydrochloride, bupivacaine, mepivacaine, prilocaine or etidocaine.

Use will preferably be made of elastomer-based microadhesive compositions containing hydrocolloids which, for a total of 100% by weight, comprise:

0.05% to 1% by weight of antioxidant;
10% to 60% by weight of tackifying resin;
2% to 20%, preferably from 12% to 16%, by weight of sodium carboxymethylcellulose;
10% to 65% by weight of a plasticizing mineral oil;
5% to 25% by weight of a poly(styrene-ethylene-butylene-styrene) or poly(styrene-ethylene-propylene-styrene) triblock polymer; and
1% to 15% by weight of a copolymer consisting of a salt of 2-methyl-2-[(1-oxo-2-propenyl)amino]-1-propanesulfonic acid and of the 2-hydroxyethyl ester of propenoic acid.

Another hydrocolloid elastomer composition may comprise, for a total of 100% by weight:

0.05% to 1% by weight of antioxidant;
2% to 20%, preferably from 12% to 16%, by weight of sodium carboxymethylcellulose;
20% to 65% by weight of a plasticizing mineral oil; and
3% to 25% by weight of a poly(styrene-ethylene-butylene-styrene) or poly(styrene-ethylene-propylene-styrene) triblock polymer.

The absorbent foam or the absorbent foam covered with an interface layer may be protected, at least on its surface intended to come into contact with the wound, with a protective film-coating which may be removed by peeling off before use of the dressing.

The peel-off protector 3 may consist of one or more parts which can be peeled off before use. This protector covers the entire surface of the absorbent foam or all of the surface of the substrate, in the case where the dressing comprises an adhesive-coated side strip.

This protector may be any material commonly used as a protector by those skilled in the art in the dressings field. It may be, for example, in the form of a film, for example a film made of a polyolefin, such as polyethylene or polypropylene, or a polyester film, but also a paper. This film is advantageously treated, on at least one of its faces, with a silicone compound such as a silane, a fluoro compound, or a fluorosilicone compound.

This protector will have to be suitable for the microadhesive nature of the interface layer. This protector will also have to be, where appropriate, suitable for the nature of the adhesive silicone gel used for the substrate if it comprises a side strip.

In the context of the present invention, the use of a two-part protector, as indicated in the figures, will in particular be preferred.

The peel-off protector preferably has a thickness of between 10 and 100 μm, for example of about 50 μm.

The product sold under the reference Silflu® M1R88001 by the company Siliconature may advantageously be used as such.

The dressing of the invention is advantageously indicated for the treatment of all exudative chronic wounds (eschar, ulcer, for instance a diabetic's foot ulcer) and acute wounds (second-degree burn, dermabrasion, trauma wound, postoperative wound).

The dressing of the invention, when it comprises an adhesive side strip, is particularly indicated for the treatment of wounds when the perilesional skin is weakened.

In the context of the present invention, the use of a dressing with rounded corners will be preferred in order to avoid premature detachment.

The dressing of the invention may be in the form of individual dressings of small size or of larger size. The dressings will be packaged individually in a sealed wrapping ensuring preservation in a sterile environment.

A subject of the present invention is also a process for manufacturing the dressing previously described, which consists in producing the substrate and in assembling the substrate to the absorbent foam. According to one embodiment, the absorbent foam is secured to the non-absorbent web, and then the assembly is assembled to the substrate by bringing the non-absorbent web into contact with the side of the support that is covered with adhesive silicone gel. For example, the absorbent foam and the non-absorbent web are heat-sealed before being calendered to the substrate.

In a first step, the substrate is produced by coating the reinforcement and assembling the coated reinforcement to the continuous film.

The silicone gel will be coated onto the reinforcement using one of the coating techniques commonly employed by those skilled in the art.

According to the preferred version of the present invention, the silicone gel is coated onto the two faces of the reinforcement, which is assembled to the continuous film even though the crosslinking of the gel is not complete, so as to ensure cohesion between the film and the openwork reinforcement. In this embodiment, no adhesive is necessary to make the reinforcement adhere to the film that is impermeable to liquids, but permeable to water vapor.

In this version, the substrate can be manufactured according to the succession of steps that follow:

the reinforcement is covered on both its faces with a mixture of the silicone gel precursors,
the reinforcement is assembled to the film, for example by calendering, and
the crosslinking of the silicone gel is brought about or accelerated once the reinforcement and the film have been assembled, by placing, for example, the substrate in an oven.

The reinforcement is, for example, immersed in the mixture of the silicone gel precursors, and then wrung in a lamination station between two rollers. A blower makes it possible to reconstitute the openings of the reinforcement in order to remove the surplus silicone gel.

In another version, the silicone gel is coated onto one of the two faces of the reinforcement, and the other face is secured to the continuous film via an adhesive. It can also be secured by heat, ultrasound or high frequency, and, in this case, the reinforcement and/or the continuous film may be thermoplastic, so as to heat-seal them.

The substrate may be protected by covering its adhesive face with a protective layer or film-coating. This protective layer may be, for example, paper or a polyester film.

In a second step, the non-absorbent web is secured to the absorbent foam. A reel of foam and a reel of non-absorbent web are unwound and then relaxed, before being superposed. The web and the foam are secured together only along their periphery via heat, ultrasound, high frequency or with an adhesive. The heat sealing is, for example, performed along the entire periphery of the pieces of foam, preferably via heat or high frequency. The sealing temperature will, for example, be between 80 and 150° C., more preferably between 90 and 120° C., in particular about 110° C. The securing of the web and of the foam is carried out, preferably along the periphery of the foam only, for example over a width of from 1 to 3 mm. Stripping is then carried out, which makes it possible to selectively cut the foam along its thickness, without cutting the web, preferably in the shape of squares.

The foam secured to the web is then assembled to the substrate previously manufactured in a lamination station, by applying a set pressure ranging from 0 to 10 bar, preferably from 0 to 6 bar. The lamination station is advantageously a drawing station.

Before carrying out the cutting, the substrate/web/foam assembly is covered, on the side of the absorbent foam intended to come into contact with the wound, with a protective film-coating which may be removed by peeling off before use of the dressing.

If the absorbent layer was previously covered with an interface layer and with a temporary peel-off protector, said temporary protector will be removed in order to cover the substrate/web/foam/interface layer assembly, on the side of the interface layer intended to come into contact with the wound, with a protective film-coating which may be removed by peeling off before use of the dressing.

When it is desired to secure the non-absorbent web to the foam with an adhesive, the non-absorbent web which has been unwound and relaxed is coated with adhesive before being calendered with the layer of foam. Stripping is then carried out, followed by securing of the assembly to the substrate under the same conditions as those previously described.

According to one embodiment, when the dressing comprises an absorbent nonwoven, the unwound and relaxed materials originating from a reel of foam, from a reel of non-absorbent web and from a reel of absorbent nonwoven will be superposed. All of the three layers will undergo two successive stripping steps in order to cut the absorbent nonwoven to a size smaller than that of the foam. If the nonwoven comprises particles of superabsorbent polymer, it is preferable to heat-seal the web and the absorbent foam.

Once the web and the absorbent foam have been secured to one another, the assembly is preferably assembled to the substrate by the same lamination process as that previously described. The choice of a non-absorbent web in accordance with the present invention advantageously makes it possible to assemble the substrate and the web without it being necessary to have recourse to an acrylic adhesive as in the prior art. The substrate and the non-absorbent web remain connected together when the used dressing is removed, or detached from the skin when it comprises an adhesive side strip.

The web and the absorbent foam are secured to one another preferably during a step which precedes the securing of the web to the substrate, in order to avoid weakening the silicone gel.

According to one embodiment, the non-absorbent web advantageously undergoes a Corona treatment, preferably just before being secured to the absorbent foam. The Corona treatment makes it possible to increase the attachment of the web to the substrate that is coated with adhesive silicone gel. In this embodiment, the web may consist of polyethylene fibers.

The absorbent foam may be covered with an interface layer, preferably before being secured to the non-absorbent web.

For example, the interface layer may comprise an elastomer-based composition and contain hydrocolloids, as previously described. This composition can be manufactured according to a hot melt process well known to those skilled in the art, by hot-blending of the various constituents at a temperature between 90 and 160° C. and preferably between 110 and 140° C. An etched cylinder is preferably dipped in the previously hot-blended composition, and then the still-hot composition is demolded and transferred onto the absorbent foam. The application of the still-hot composition onto the foam makes it possible to optimize the attachment of the interface layer. A temporary protector is then placed on the foam covered with the interface layer before carrying out the stripping step. The temporary protector is removed after the securing of the foam/web assembly to the substrate, in order to apply a peel-off protector which will be removed before the application of the dressing to the skin.

The invention is illustrated by the following example.

EXAMPLE 1

Preparation of an Absorbent Dressing

A dressing comprising a microadhesive interface layer, an absorbent foam, and airlaid nonwoven, a non-absorbent polyethylene web, a substrate that is coated with adhesive silicone gel and a peel-off protector is manufactured.

The following materials are used:

The substrate is a 40 g/m$^2$ polyester knit that is coated on both its faces and on its entire surface with an adhesive silicone gel (200 g/m$^2$), which was laminated on a polyurethane film 30 μm thick. This substrate has a thickness of about 300 μm and an MVTR of about 5000 g/m$^2$/24 hours.

The non-absorbent web is, for example, a 40 g/m$^2$ polyethylene nonwoven sold under the reference Vilmed® LSO 1040 Weiss by Freudenberg.

The absorbent foam is a 3 mm hydrophilic polyurethane foam sold by Corpura under the reference MCF 03.

An absorbent nonwoven is inserted between the web and the foam: it is an airlaid nonwoven (200 g/m$^2$) containing a superabsorbent polymer from EAM Corporation sold under the reference Novathin®.

The fluorosilicone-coated PET peel-off protector 50 microns thick is made up of two wings; it is supplied by Siliconature under the reference Silflu® M1R88001.

Preparation of the Interface Layer and Coating onto the Absorbent Foam:

The following composition, expressed as percentage by weight relative to the total weight, is prepared:

Mineral oil sold by the company Shell under the name Ondina® 919: 39.7%

Sodium salt of carboxymethylcellulose sold by the company Aqualon under the name CMC Blanose® 7H4XF: 14.8%

Poly(styrene-ethylene-butylene) block copolymer sold by the company Kraton under the name Kraton® G 1651E: 4.7%

Antioxidant sold under the name Irganox® 1010 by the company Ciba Specialty Chemicals: 0.2%

Copolymère 2-methyl-2[(1-oxo-2-propenyl)amino]-1-propanesulfonic acid salt and of the 2-hydroxyethyl ester of propenoic acid (releasing agent) sold by the company SEPPIC under the name Sepinov® EMT 10: 5%

Tackifying resin sold by the company Exxon Chemicals under the name Escorez® 5380: 35.6%.

The mineral oil, the hydrocolloid and the elastomer and then the antioxidant and the releasing agent and, finally, the tackifying resin, which were brought to a temperature of between 100 and 110° C., were introduced into an MEL G-40 blender, so as to obtain a homogeneous mixture.

The previous mixture is discontinuously coated, in an amount of 170 g/m² (±40), onto the hydrophilic polyurethane foam.

Assembling of the Layers:

The sheet of polyurethane web undergoes a Corona treatment under the following conditions.

Generator power: 570 watts

Number of electrodes/width: 3/0.25 m

Gap adjustment: 2mm

Travel speed: 2 m/minute

Before the effects of the Corona treatment have disappeared, the web and the hydrophilic polyurethane foam are sealed on just one side, over a width of 2 mm, with an Amis manual sealer; the absorbent nonwoven is then inserted between the foam and the web.

The last three sealing operations are carried out under the same conditions as previously, so as to form an 8×8 cm square, and then the edges of the assembled complex are cut off.

The substrate is cut into a 15×15 cm square and then assembled to the previous complex by calendering with a 10 kg roller, in two perpendicular directions.

The final 13×13 cm dressing is then cut out, with the corners being rounded.

The invention claimed is:

1. A dressing comprising an absorbent foam and a protective substrate that is impermeable to fluids, but permeable to water vapor,
said substrate being formed by assembling a continuous film and an openwork reinforcement that is coated, on at least one of its faces, with an adhesive silicone gel without blocking the openings in the reinforcement, said reinforcement covering the entire surface of the film,
said dressing also comprising a non-absorbent web which is inserted between said absorbent foam and said substrate, which web adheres to the adhesive silicone gel that is coated onto said reinforcement, and which is secured to the absorbent foam.

2. The dressing as claimed in claim 1, wherein the non-absorbent web has a grammage of between 15 and 50 g/m².

3. The dressing as claimed in claim 1, wherein the non-absorbent web comprises polyethylene fibers.

4. The dressing as claimed in claim 1, wherein the absorbent foam is centered on the substrate, the surface of which is greater, so as to create adhesive borders.

5. The dressing as claimed in claim 1, wherein the absorbent foam is a hydrophilic polyurethane foam.

6. The dressing as claimed in claim 1, wherein the grammage of the adhesive silicone gel is between 100 and 500 g/m².

7. The dressing as claimed in claim 1, wherein the absorbent foam is covered, on the surface adapted to face a wound, with a discontinuous interface layer comprising an elastomer, a plasticizer and hydrocolloids.

8. The dressing as claimed in claim 1, wherein the openwork reinforcement is a knit that is coated with adhesive silicone gel on both its faces and on its entire surface without blocking the openings of the knit.

9. The dressing as claimed in claim 1, wherein the openwork reinforcement is a perforated film that is coated with adhesive silicone gel on one of its faces, without blocking the perforations of the film.

10. The dressing as claimed in claim 1, wherein an absorbent nonwoven is inserted between the non-absorbent web and the absorbent foam.

11. A method comprising applying a dressing on a wound, wherein the dressing comprises an absorbent foam and a protective substrate that is impermeable to fluids, but permeable to water vapor,
said substrate being formed by assembling a continuous film and an openwork reinforcement that is coated, on at least one of its faces, with an adhesive silicone gel without blocking the openings in the reinforcement, said reinforcement covering the entire surface of the film,
said dressing also comprising a non-absorbent web which is inserted between said absorbent foam and said substrate, which web adheres to the adhesive silicone gel that is coated onto said reinforcement, and which is secured to the absorbent foam.

12. The method of claim 11, wherein the wound is an exudative chronic wound.

13. The method of claim 12, wherein the exudative chronic wound is an eschar, an ulcer or an acute wound.

14. The method of claim 13, wherein the ulcer is a diabetic's foot ulcer.

15. The method of claim 13, wherein the acute wound is a second-degree burn, a dermabrasion, a trauma wound or a post-operative wound.

16. A process for manufacturing a dressing as claimed in claim 1, comprising, producing the substrate, securing the non-absorbent web and the foam to form an assembly, and then assembling the assembly to the substrate.

17. The process as claimed in claim 16, wherein the web and the foam are secured together only along their periphery via heat, ultrasound, high frequency or with an adhesive.

18. The process as claimed in claim 16, wherein the substrate is assembled to the assembly comprising the web and the foam in a lamination station by applying a pressure ranging from 0 to 10 bar.

19. The process as claimed in claim 16, wherein the non-absorbent web undergoes a Corona treatment, just before being secured to the foam.

* * * * *